(12) United States Patent
Moran et al.

(10) Patent No.: US 11,975,144 B2
(45) Date of Patent: May 7, 2024

(54) EMERGENCY VENTILATOR SYSTEM

(71) Applicant: Ator Labs, Inc., Panama City Beach, FL (US)

(72) Inventors: Robert Nickell Moran, Panama City Beach, FL (US); Christopher Whittle, Panama City Beach, FL (US); Francisco Hernandez, Panama City Beach, FL (US); David Cowgill, Panama City Beach, FL (US); Sieggy Bennicoff-Yundt, Panama City Beach, FL (US); Joshua Lamb, Panama City Beach, FL (US)

(73) Assignee: Ator Labs, Inc., Panama City Beach, FL (US)

( * ) Notice: Subject to any disclaimer, the term of this patent is extended or adjusted under 35 U.S.C. 154(b) by 385 days.

(21) Appl. No.: 17/226,938

(22) Filed: Apr. 9, 2021

(65) Prior Publication Data

US 2021/0316095 A1    Oct. 14, 2021

Related U.S. Application Data

(60) Provisional application No. 63/007,685, filed on Apr. 9, 2020.

(51) Int. Cl.
*A61M 16/00*      (2006.01)
*A61M 16/08*      (2006.01)
(Continued)

(52) U.S. Cl.
CPC ...... *A61M 16/0072* (2013.01); *A61M 16/024* (2017.08); *A61M 16/1005* (2014.02);
(Continued)

(58) Field of Classification Search
CPC .............. A61M 16/00; A61M 16/0057; A61M 16/0072; A61M 16/0075; A61M 16/0078;
(Continued)

(56) References Cited

U.S. PATENT DOCUMENTS 3,599,633 A * 8/1971 Beasley ................ A61M 16/00
                                                   128/205.18
3,730,180 A * 5/1973 Davison ............ A61M 16/0012
                                                   128/204.24
(Continued)

FOREIGN PATENT DOCUMENTS

WO    WO-2021203189 A1 * 10/2021

OTHER PUBLICATIONS

Maloney, Dan; "Mechanisms: Lead Screws and Ball Screws", published on Hackaday at https://web.archive.org/web/20190519012129/https://hackaday.com/2018/11/13/mechanisms-lead-screws-and-ball-screws with date May 18, 2019.*

*Primary Examiner* — Joseph D. Boecker
(74) *Attorney, Agent, or Firm* — Shumaker, Loop & Kendrick, LLP; Patrick B. Horne

(57) ABSTRACT

An emergency ventilation system ventilates a patient and includes a chamber housing defining a breathing chamber; a piston; and a motor operably connected to the piston. The motor applies an exhalation force to move the piston in an exhalation direction applies an inhalation force to move the piston in an inhalation direction. The piston increases air in the breathing chamber as the exhalation force is applied and decreases air in the breathing chamber as the inhalation force is applied. An exhalation check valve allows airflow from the air source to the breathing chamber and not to allow airflow from the breathing chamber to the air source as the inhalation force is applied. An inhalation check valve allows airflow from the breathing chamber to the air output and not (Continued)

to allow airflow from the air output to the breathing chamber as the exhalation force is applied.

9 Claims, 15 Drawing Sheets

(51) Int. Cl.
  *A61M 16/10* (2006.01)
  *A61M 16/12* (2006.01)
  *A61M 16/20* (2006.01)
(52) U.S. Cl.
  CPC ........ *A61M 16/125* (2014.02); *A61M 16/208* (2013.01); *A61M 2016/0027* (2013.01); *A61M 16/0858* (2014.02); *A61M 2016/1025* (2013.01); *A61M 2202/0208* (2013.01); *A61M 2205/106* (2013.01); *A61M 2207/00* (2013.01)
(58) Field of Classification Search
  CPC .. A61M 16/024; A61M 16/12; A61M 16/122; A61M 16/125; A61M 16/208; A61M 2207/00; A61M 2016/0027; A61M 2016/1025
  See application file for complete search history.

(56) References Cited

U.S. PATENT DOCUMENTS

| | | | | |
|---|---|---|---|---|
| 4,493,614 | A * | 1/1985 | Chu | F04B 35/06 92/33 |
| 5,531,221 | A * | 7/1996 | Power | A61M 16/0072 417/259 |
| 5,664,560 | A * | 9/1997 | Merrick | A61M 16/12 417/259 |
| 5,673,689 | A * | 10/1997 | Power | A61M 16/0057 128/203.12 |
| 6,234,170 | B1 * | 5/2001 | Bergkvist | A61M 16/0063 128/205.18 |
| 2010/0139660 | A1 * | 6/2010 | Adahan | A61M 16/206 128/205.24 |
| 2010/0170512 | A1 * | 7/2010 | Kuypers | A61M 16/0069 128/204.23 |
| 2010/0313898 | A1 * | 12/2010 | Richard | A61M 16/0666 128/200.24 |

* cited by examiner

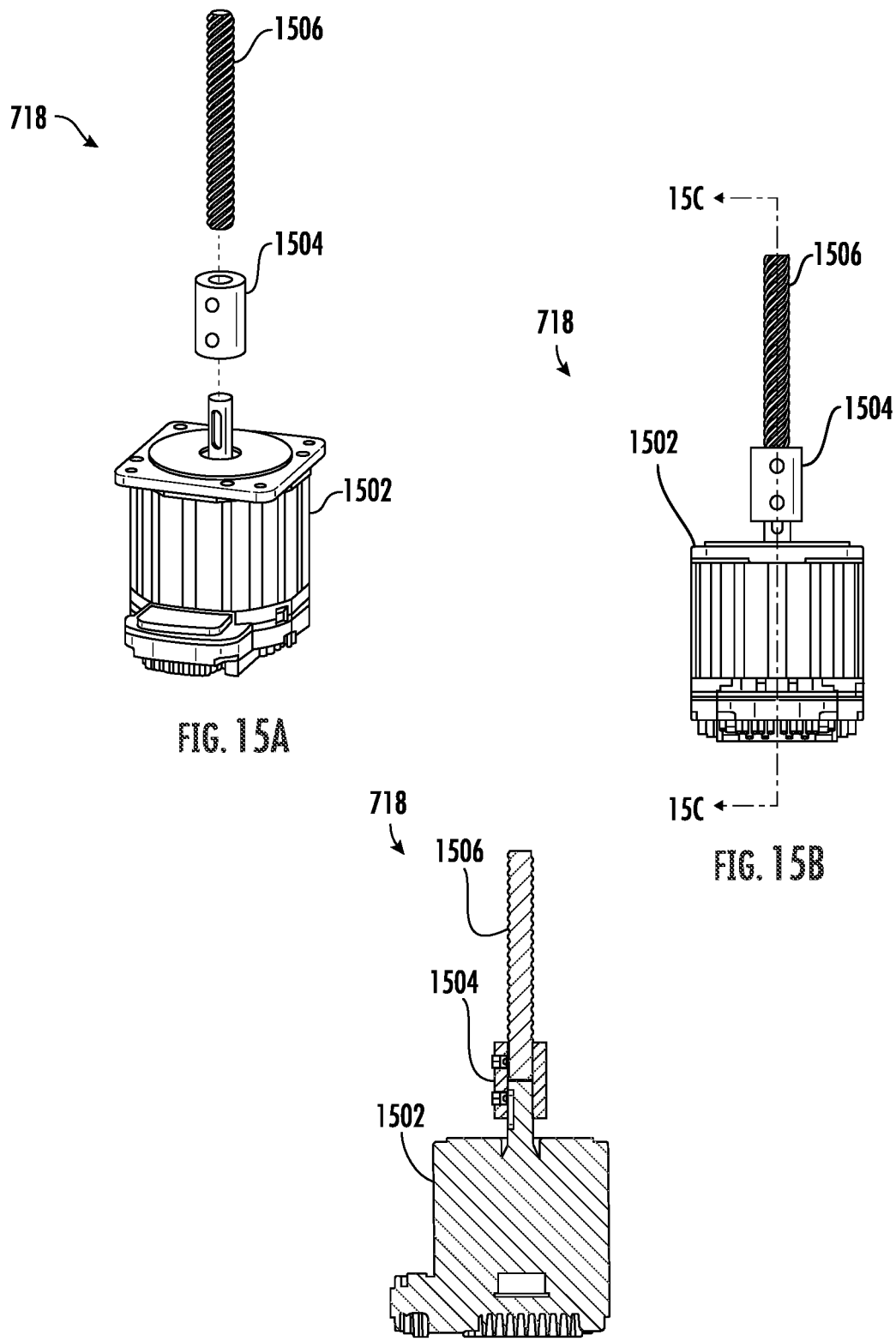

EMERGENCY VENTILATOR SYSTEM

CROSS-REFERENCE TO RELATED APPLICATIONS

This application is a non-provisional application tracing priority and claiming benefit to U.S. Provisional Application No. 63/007,685, filed Apr. 9, 2020, entitled "EMERGENCY VENTILATOR SYSTEM", the entirety of which is expressly incorporated herein by reference.

FIELD

This invention relates generally to the field of ventilators, and more particularly embodiments of the invention relate to an emergency ventilator system.

BACKGROUND

Mechanical ventilators are historically large, cumbersome, and expensive and time-consuming to build.

BRIEF SUMMARY

Embodiments of the present invention address the above needs and/or achieve other advantages by providing apparatuses and methods for emergency ventilation.

Embodiments of the invention provide an emergency ventilator system for mechanical ventilation of a patient. The emergency ventilator system includes a chamber housing defining a breathing chamber; a piston; a motor operably connected to the motor, the motor configured to apply an exhalation force to move the piston in an exhalation direction corresponding to the patient's exhalation and to apply an inhalation force to move the piston in an inhalation direction corresponding to the patient's inhalation; wherein the piston increases an amount of air in the breathing chamber as the exhalation force is applied and decreases the amount of air in the breathing chamber as the inhalation force is applied; at least one exhalation check valve disposed between an air source and the breathing chamber, the at least one exhalation check valve configured to allow airflow from the air source to the breathing chamber as the exhalation force is applied and not to allow airflow from the breathing chamber to the air source as the inhalation force is applied; and at least one inhalation check valve disposed between the breathing chamber and an air output, the at least one inhalation check valve configured to allow airflow from the breathing chamber to the air output as the inhalation force if applied and not to allow airflow from the air output to the breathing chamber as the exhalation force is applied.

In some embodiments, each of the chamber housing and piston are generated by a three-dimensional (3D) printing method, thereby enabling a quick manufacture of the emergency ventilator system.

In some embodiments, the at least one exhalation check valve comprises at least a first exhalation check valve and a second exhalation valve connected in series with one another between the air source and the breathing chamber.

In some embodiments, the at least one inhalation check valve comprises at least a first inhalation check valve and a second inhalation check valve connected in series with one another between the breathing chamber and the air output.

In some embodiments, the emergency ventilator system includes an oxygen sensor disposed between the first inhalation check valve and the second inhalation check valve.

In some embodiments, the emergency ventilator system also includes an oxygen addition port for receiving oxygen and infusing the airflow with the received oxygen.

In some embodiments, the emergency ventilator system includes an oxygen sensor disposed between the first inhalation check valve and the second inhalation check valve; and an oxygen addition port disposed between the first inhalation check valve and the second inhalation check valve, the oxygen addition port for receiving oxygen and infusing the airflow with the received oxygen. In some such embodiments, the oxygen sensor senses an oxygen level of the airflow and the oxygen addition port infuses oxygen into the airflow based at least in part on the oxygen level sensed by the oxygen sensor.

In some embodiments, the emergency ventilator system includes an exterior housing configured to enclose the motor, piston, and chamber housing. In some such embodiments, the exterior housing is generated by a three-dimensional (3D) printing method, thereby enabling a quick manufacture of the emergency ventilator system.

In some embodiments, the emergency ventilator system also includes a rolling seal disposed between the piston and sides of the chamber housing, the rolling seal configured to seal the chamber housing to ensure the breathing chamber retains air pressure necessary to generate air flow through the check valves as exhalation force is applied and as the inhalation force is applied.

In some embodiments, the emergency ventilator system includes a lead screw operatively connected to the motor and configured to transfer the exhalation force and the inhalation force to the piston.

In some embodiments, the emergency ventilator system also includes a pressure transducer disposed between the second inhalation check valve and the air output, the pressure transducer for measuring an output pressure of the emergency ventilator system; and an electrical connection configured to operably connect the motor, the oxygen sensor, and the pressure transducer to a processor configured to control operation of the emergency ventilator system in order to replicate natural ventilation of the patient.

According to embodiments of the invention, a method for providing emergency ventilation for a patient includes generating an exterior housing, a chamber housing, and a piston using a three dimensional (3D) printing process; building an emergency ventilator system using the 3D printed exterior housing, the chamber housing, and the piston; and providing mechanical ventilation for the patient using the emergency ventilator system.

According to embodiments of the invention, a method for providing emergency mechanical ventilation for a patient includes providing an emergency ventilator system comprising a three-dimensional (3D) printed exterior housing, chamber housing, and piston; and providing mechanical ventilation for the patient using the emergency ventilator system.

The features, functions, and advantages that have been discussed may be achieved independently in various embodiments of the present invention or may be combined in yet other embodiments, further details of which can be seen with reference to the following description and drawings.

BRIEF DESCRIPTION OF THE SEVERAL VIEWS OF THE DRAWINGS

Figure 1A:
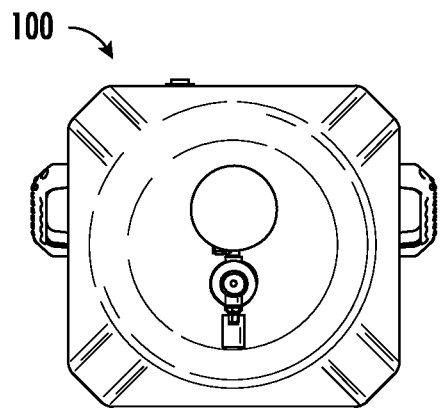
Figure 1B:
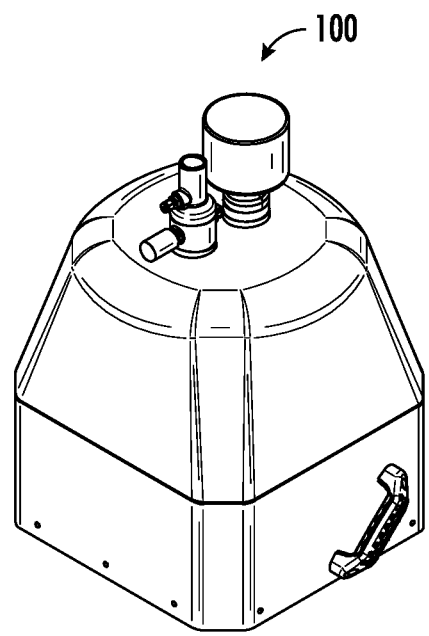
Figure 1C:
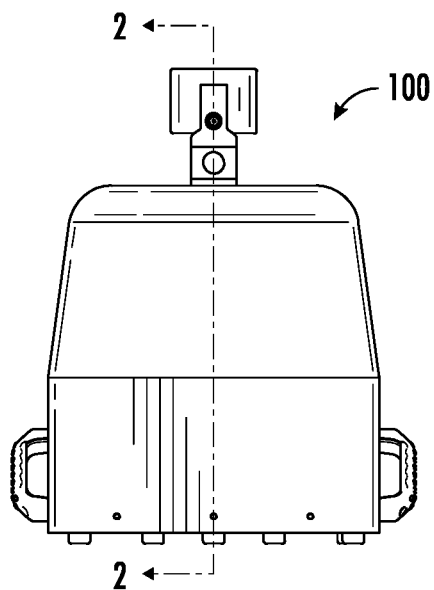
Figure 1D:
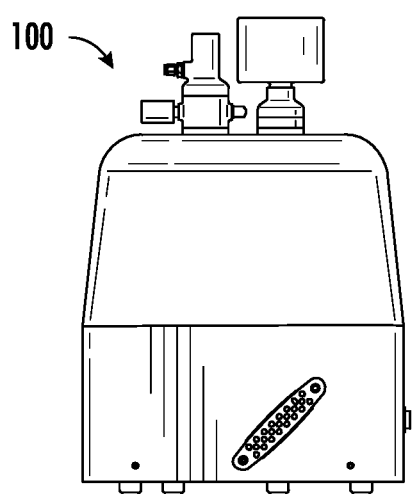
Figure 2:
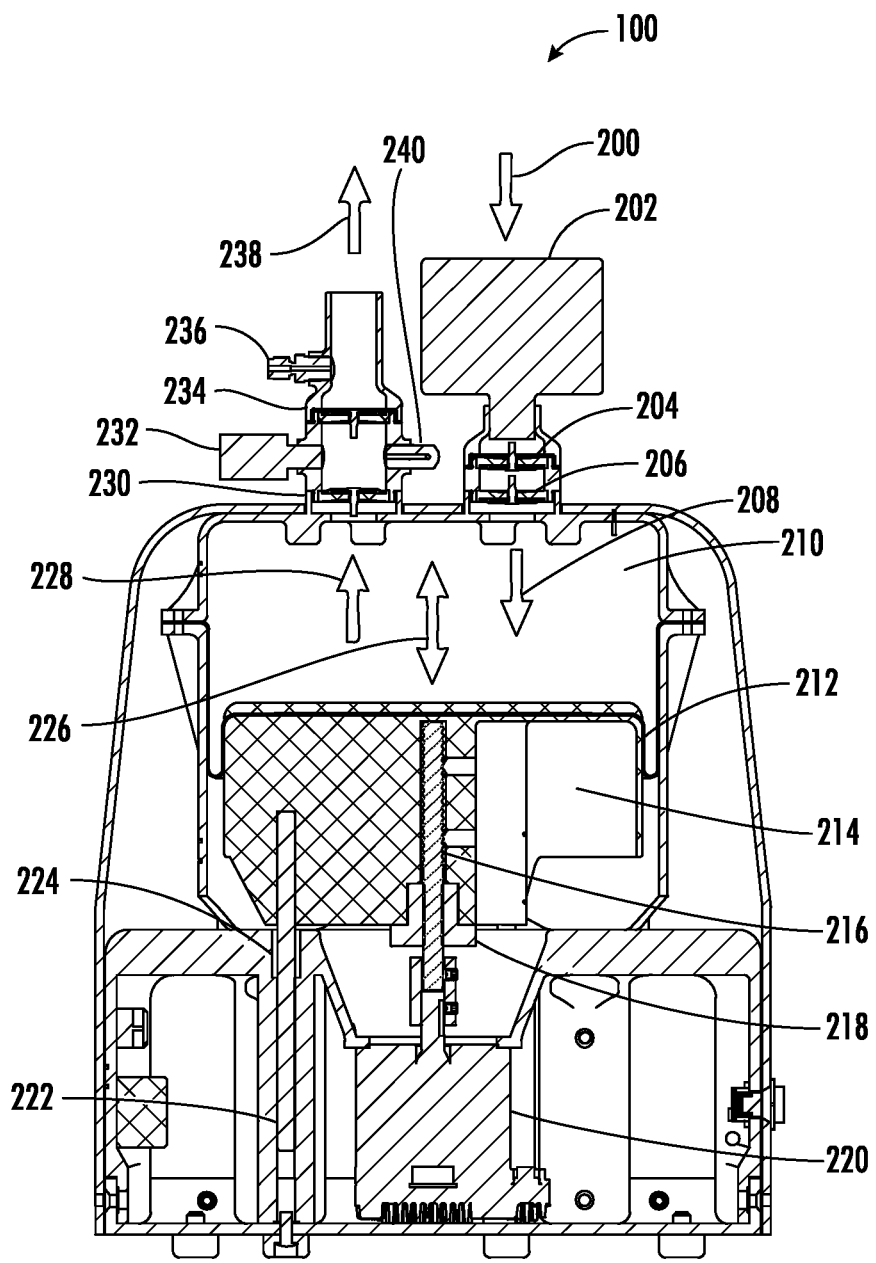
Figure 4:
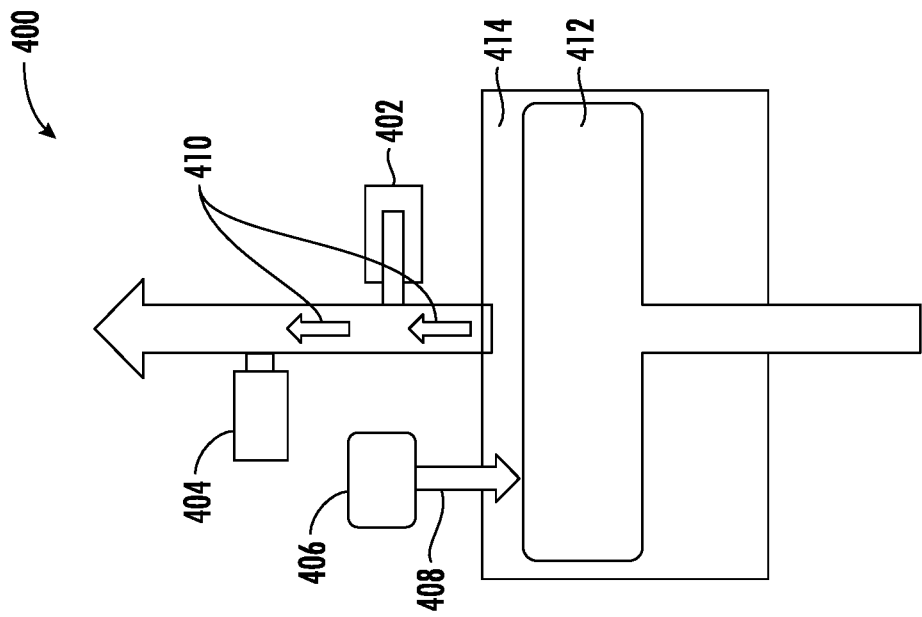
Figure 3:
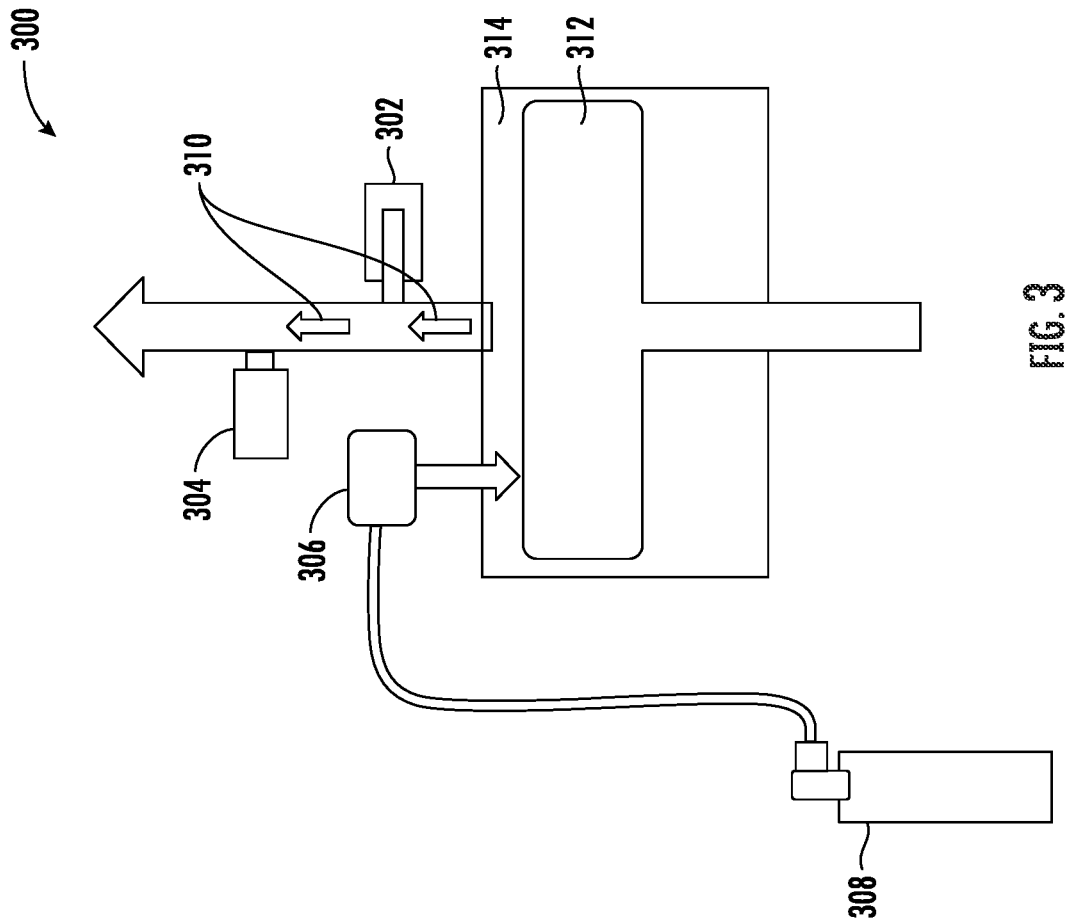
Figure 5:
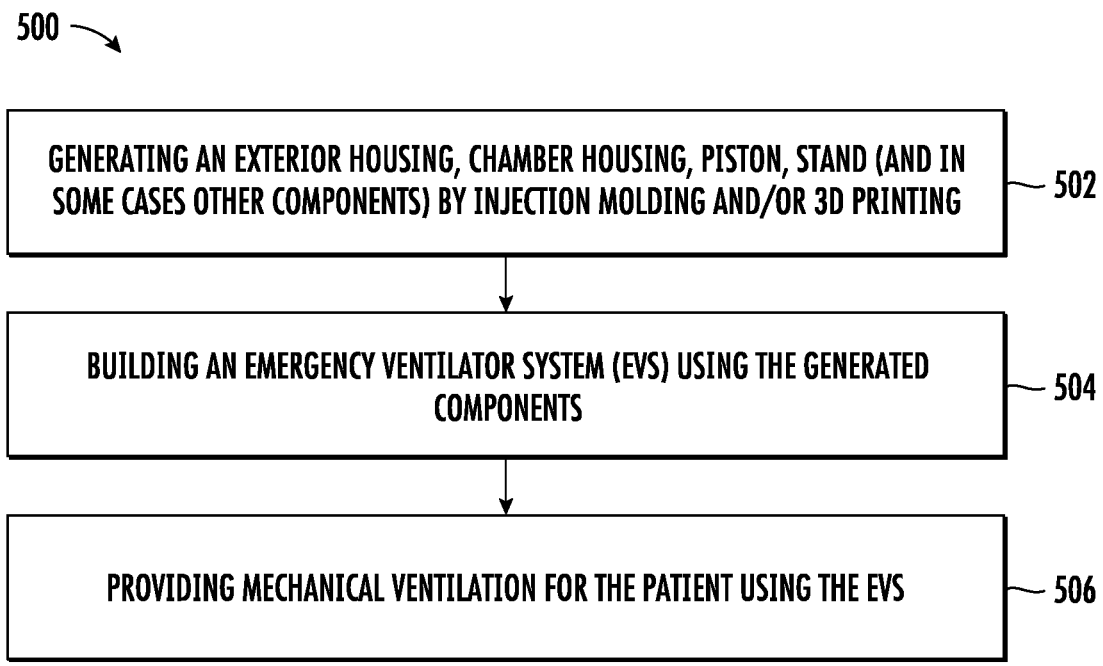
Figure 6:
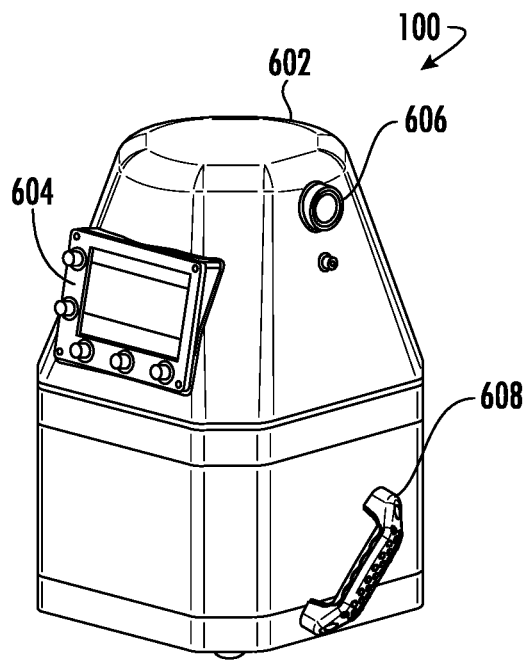
Figure 7:
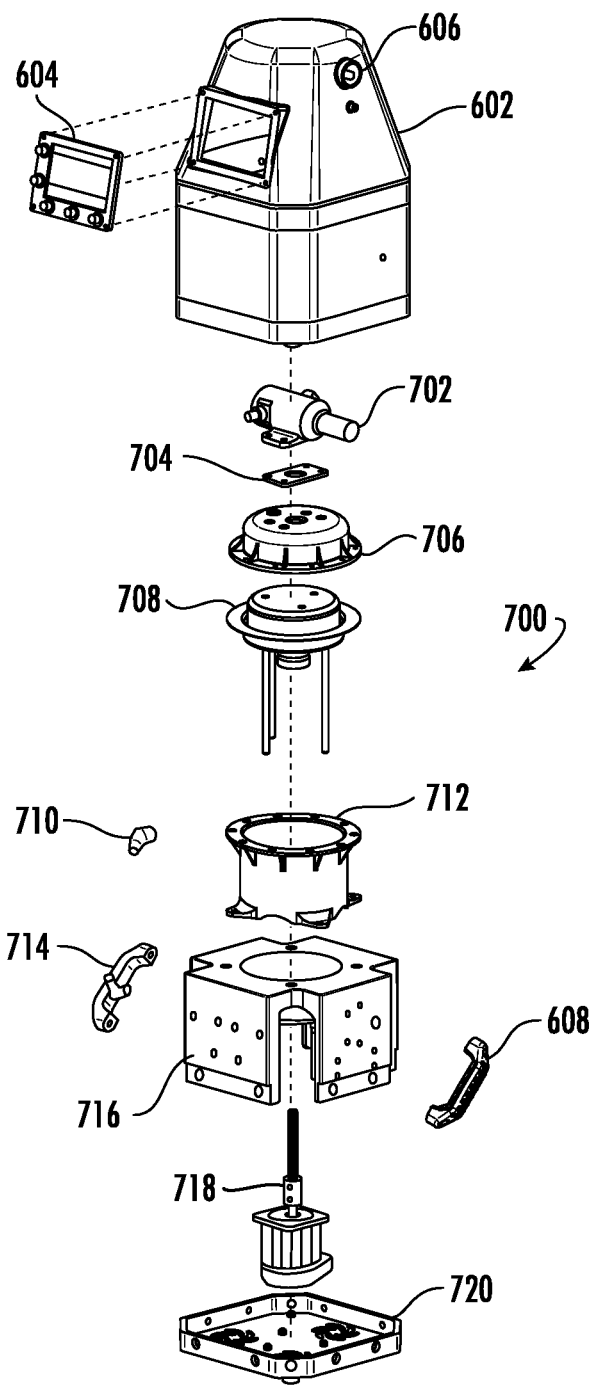
Figure 8:
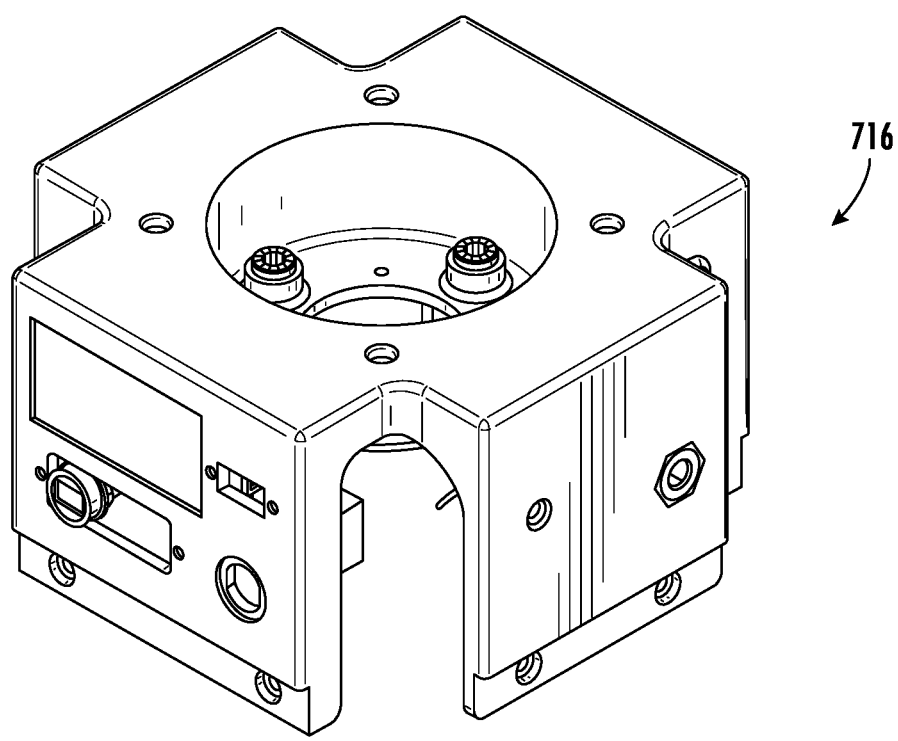
Figure 9A:
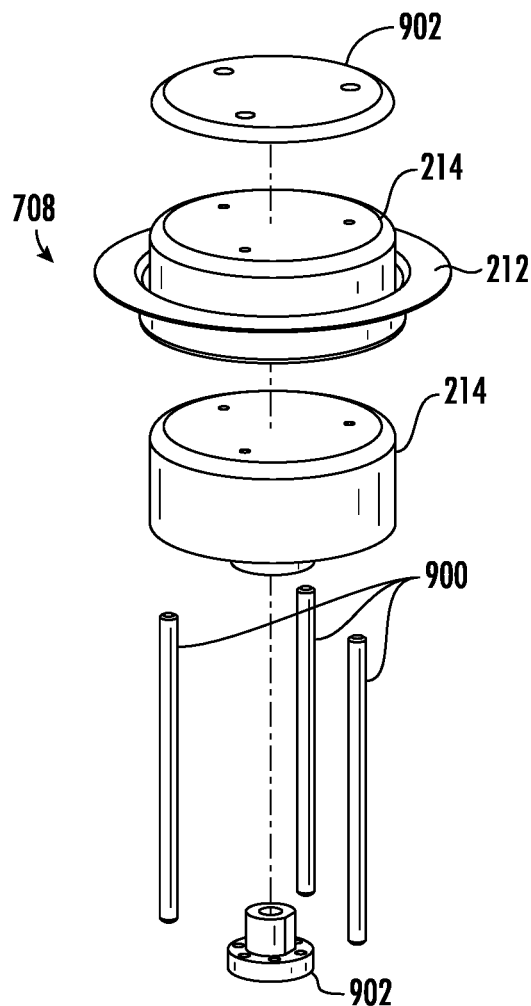
Figure 9B:
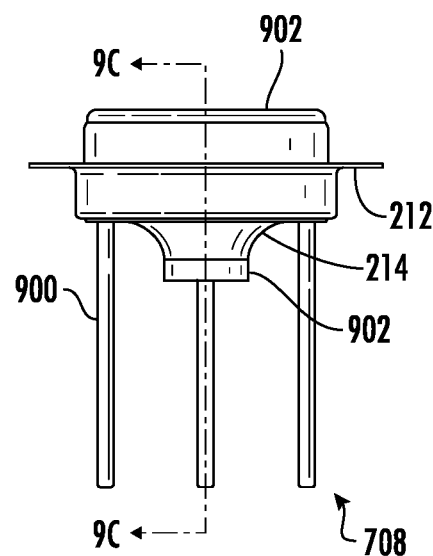
Figure 9C:
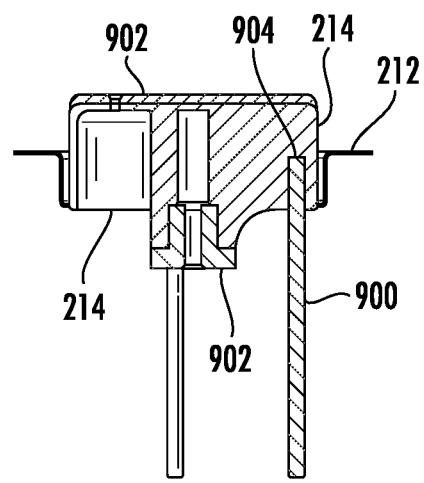
Figure 10A:
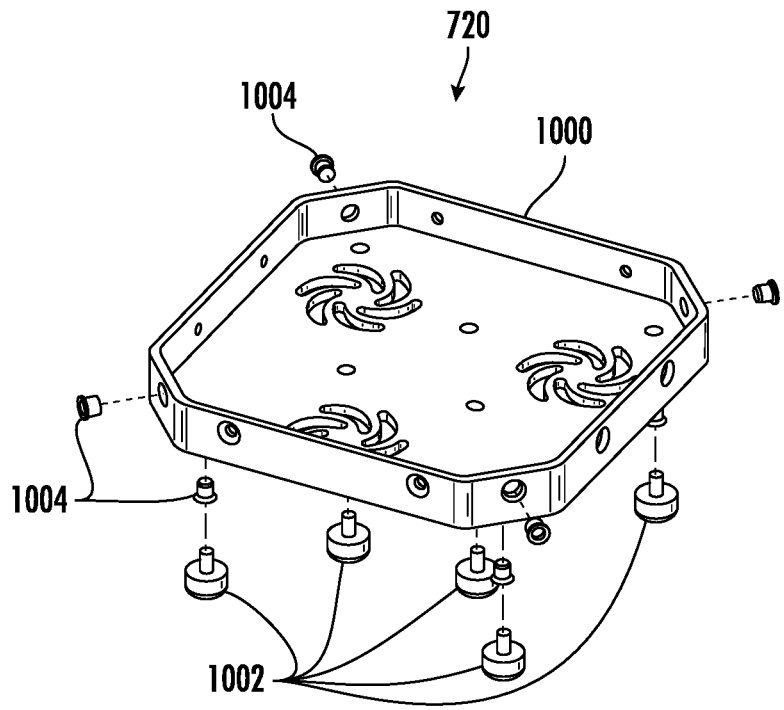
Figure 10B:
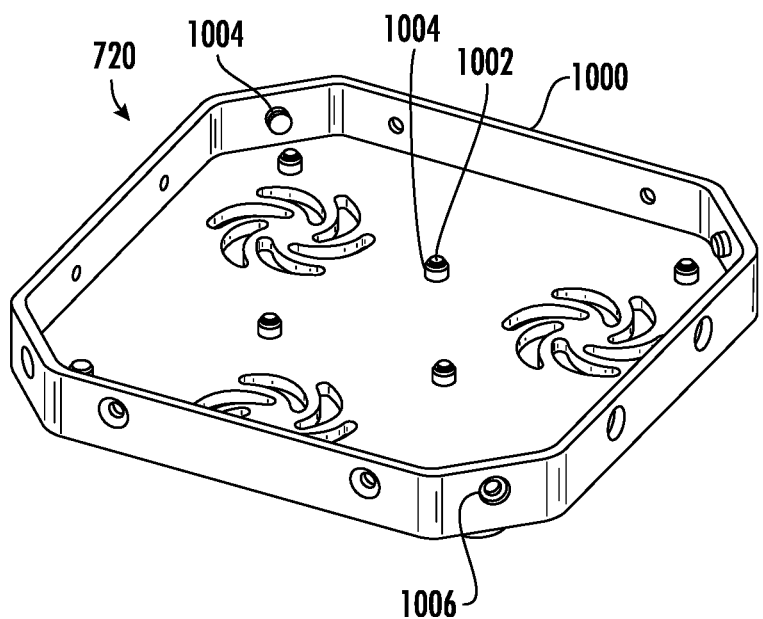
Figure 11A:
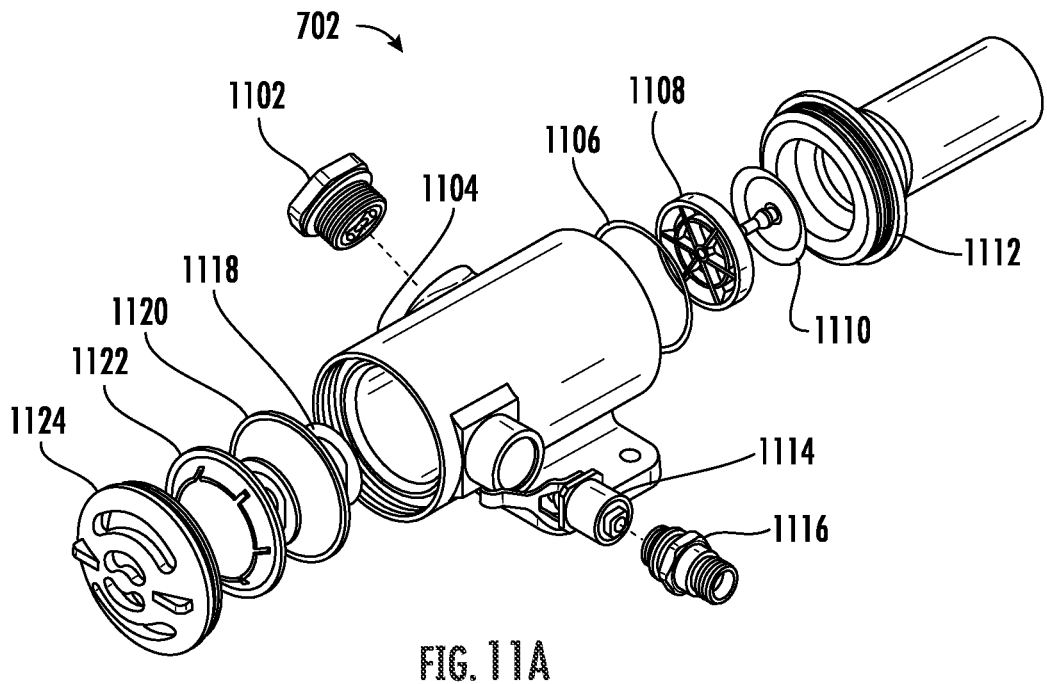
Figure 11B:
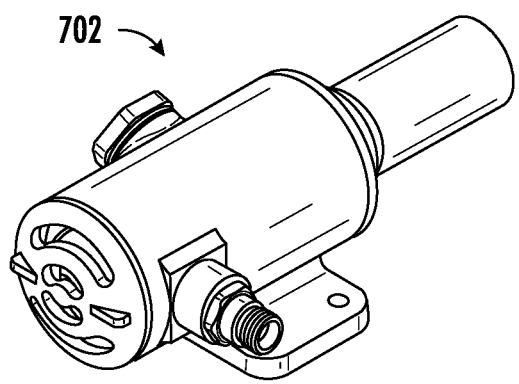
Figure 12A:
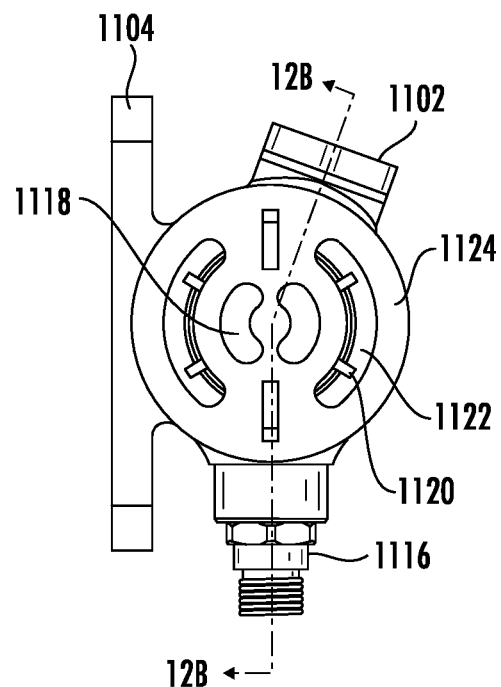
Figure 12B:
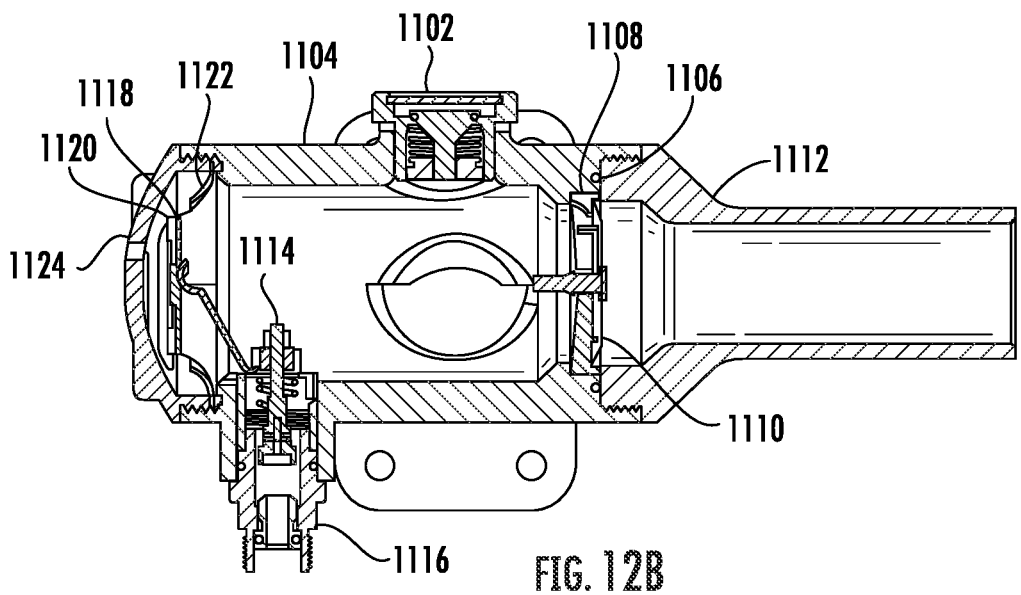
Figure 13:
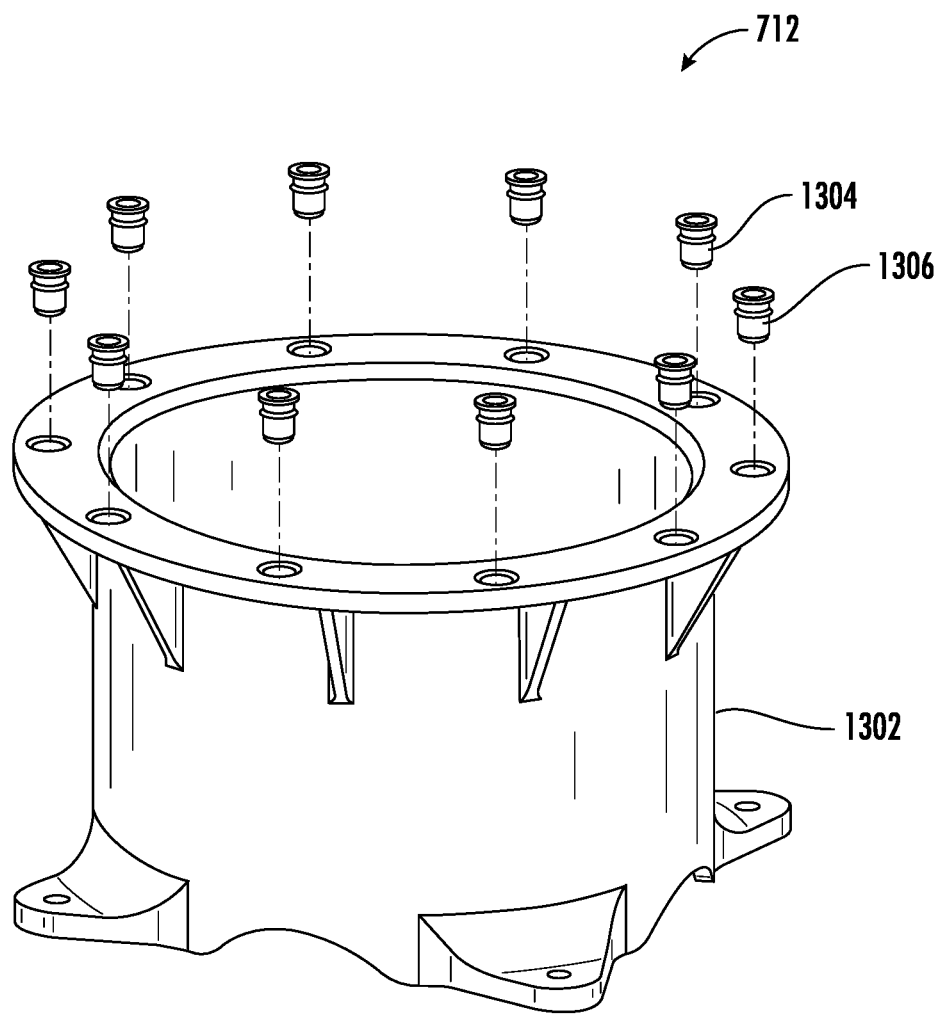
Figure 14A:
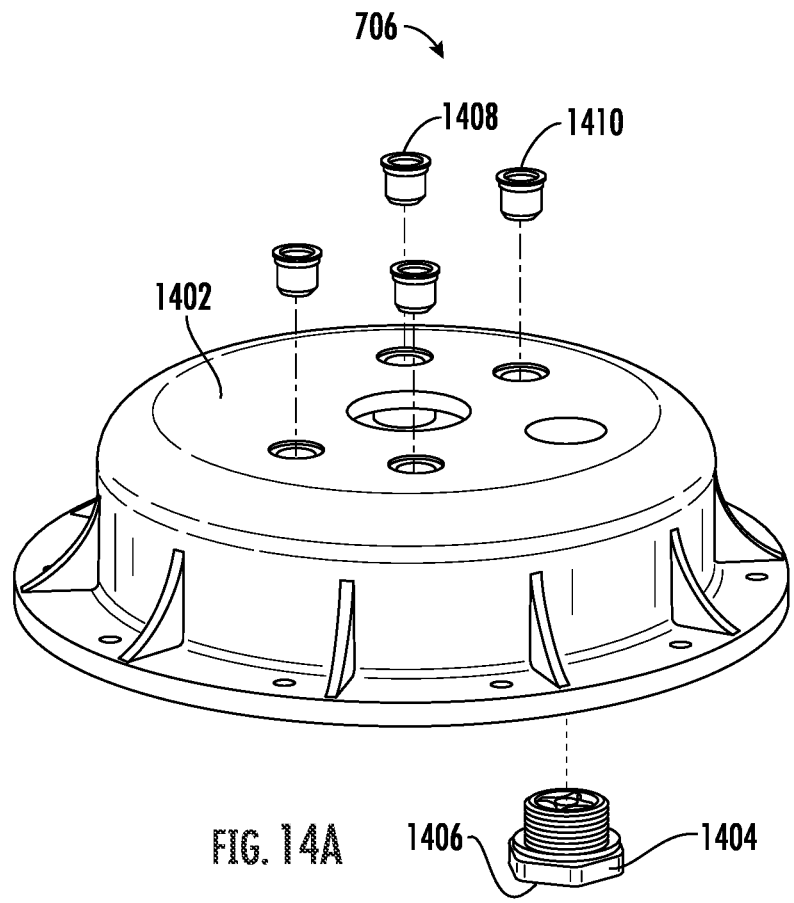
Figure 14B:
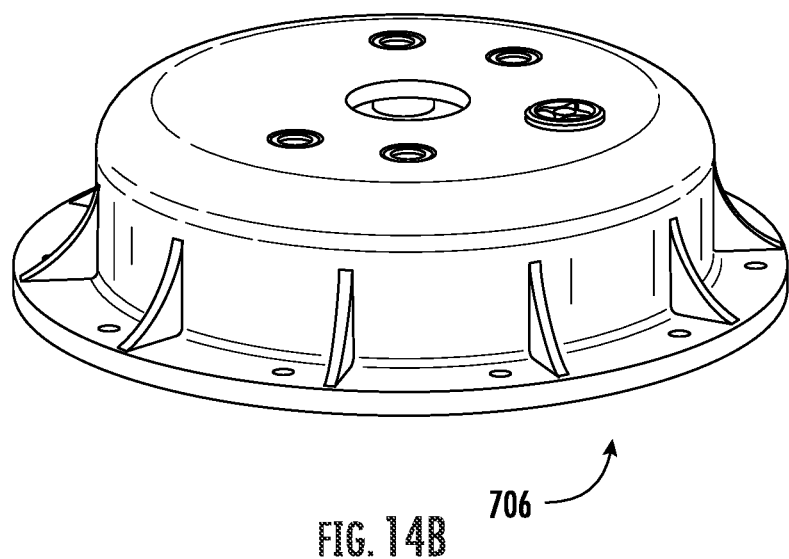
Figure 16A:
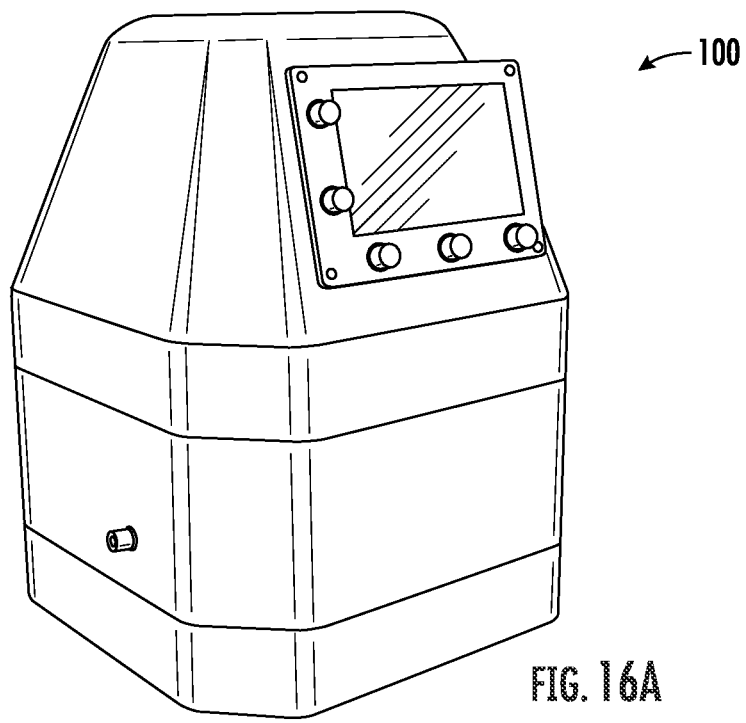
Figure 16B:
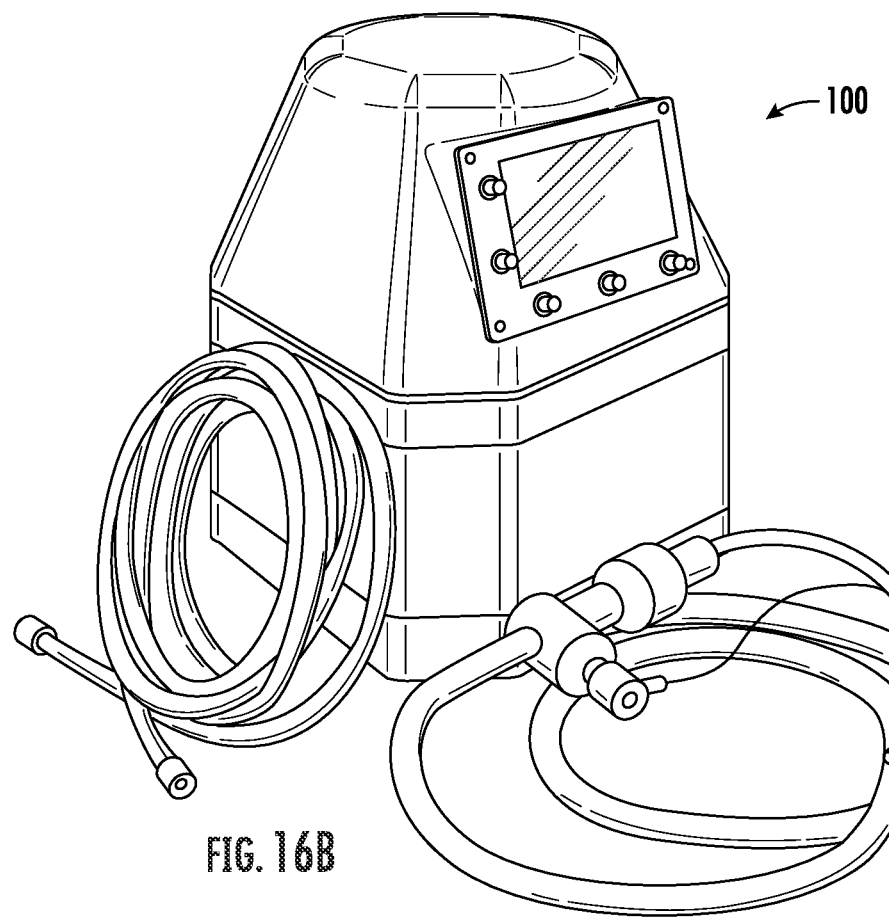
Figure 16C:
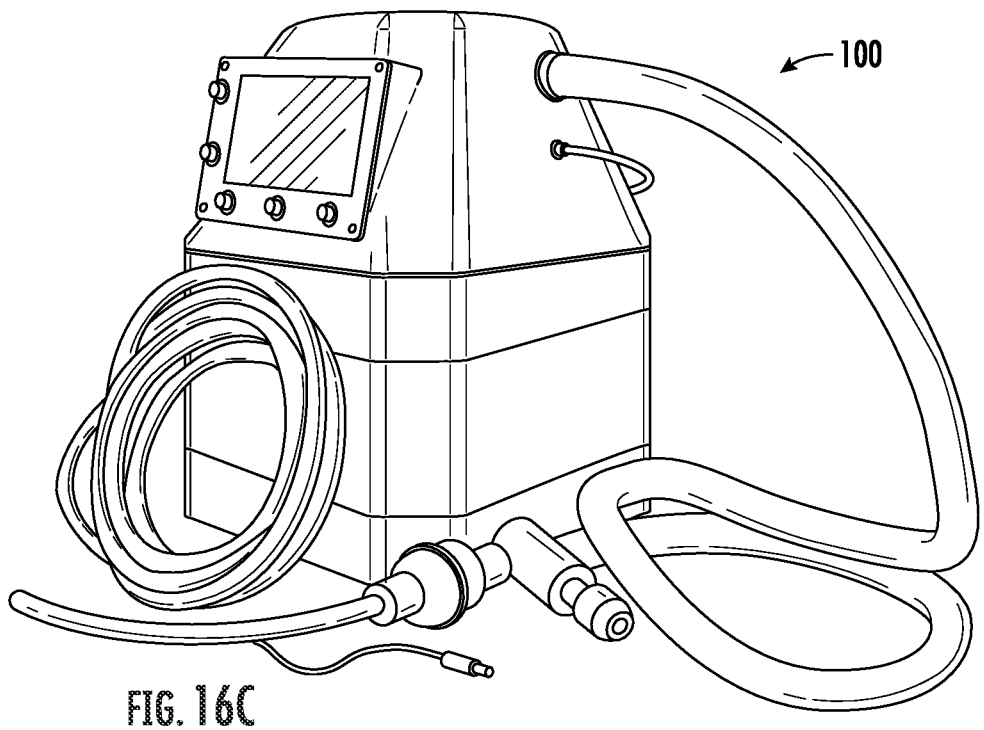
Figure 16D:
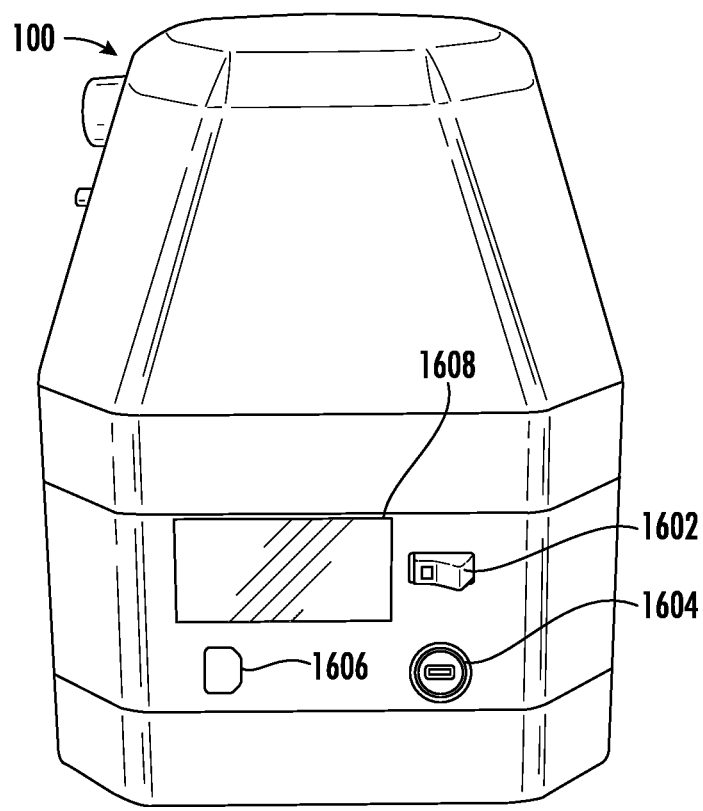

Having thus described embodiments of the invention in general terms, reference will now be made to the accompanying drawings, wherein:

FIGS. 1A, 1B, 1C, and 1D illustrate top, perspective, front, and side views, respectively, of an emergency ventilator system (EVS), in accordance with one embodiment of the present invention;

FIG. 2 illustrates cross-section 2-2 taken from FIG. 1C of the EVS, in accordance with one embodiment of the present invention;

FIG. 3 is a high level diagram illustrating a 100% oxygen mode for the EVS, in accordance with one embodiment of the present invention;

FIG. 4 is a high level diagram illustrating an oxygen enriched air mode for the EVS, in accordance with one embodiment of the present invention;

FIG. 5 is a flowchart illustrating a method for building an EVS and providing patient mechanical ventilation, in accordance with one embodiment of the present invention;

FIG. 6 is a full assembly diagram of an embodiment of the EVS;

FIG. 7 is an exploded view illustrating the sub-assemblies of an embodiment of the EVS;

FIG. 8 is a diagram of an embodiment of the stand sub-assembly of the EVS;

FIG. 9A is an exploded view illustrating an embodiment of the piston sub-assembly of the EVS;

FIG. 9B is a side view illustrating an embodiment of the piston sub-assembly of the EVS;

FIG. 9C is cross-section 9C-9C taken from FIG. 9B, in accordance with one embodiment of the invention;

FIG. 10A is an exploded view illustrating an embodiment of a baseplate sub-assembly of the EVS;

FIG. 10B is a diagram illustrating an embodiment of the baseplate sub-assembly of the EVS;

FIG. 11A is an exploded view illustrating an embodiment of a regulator sub-assembly of the EVS;

FIG. 11B is a diagram illustrating an embodiment of the regulator sub-assembly of the EVS;

FIG. 12A is an end view of an embodiment of the regulator sub-assembly of the EVS;

FIG. 12B is cross-section 12B-12B taken from FIG. 12A;

FIG. 13 is an exploded view of an embodiment of the cylinder-riser sub-assembly of the EVS;

FIG. 14A is an exploded view of an embodiment of the cylinder lid sub-assembly of the EVS;

FIG. 14B is a diagram illustrating an embodiment of the cylinder lid sub-assembly of the EVS;

FIG. 15A is an exploded view of an embodiment of a motor sub-assembly of the EVS;

FIG. 15B is a side view of an embodiment of the motor sub-assembly of the EVS;

FIG. 15C is cross-section 15C-15C taken from FIG. 15B;

FIG. 16A is a perspective view of an embodiment of a fully assembled EVS;

FIG. 16B is a perspective view of the embodiment of the fully assembled EVS of FIG. 16A with attachments;

FIG. 16C is a rear perspective view of the embodiment of the fully assembled EVS of FIG. 16A; and FIG. 16D is a rear view of the embodiment of the fully assembled EVS of FIG. 16A.

DETAILED DESCRIPTION OF EMBODIMENTS OF THE INVENTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

The present invention provides an emergency ventilator system that can be manufactured quickly in crises such as the COVID-19 pandemic. The emergency ventilator system, according to embodiments of the invention, provides for mechanical ventilation of a patient. The emergency ventilator system includes a chamber housing defining a breathing chamber; a piston; a motor operably connected to the motor, the motor configured to apply an exhalation force to move the piston in an exhalation direction corresponding to the patient's exhalation and to apply an inhalation force to move the piston in an inhalation direction corresponding to the patient's inhalation; wherein the piston increases an amount of air in the breathing chamber as the exhalation force is applied and decreases the amount of air in the breathing chamber as the inhalation force is applied; at least one exhalation check valve disposed between an air source and the breathing chamber, the at least one exhalation check valve configured to allow airflow from the air source to the breathing chamber as the exhalation force is applied and not to allow airflow from the breathing chamber to the air source as the inhalation force is applied; and at least one inhalation check valve disposed between the breathing chamber and an air output, the at least one inhalation check valve configured to allow airflow from the breathing chamber to the air output as the inhalation force if applied and not to allow airflow from the air output to the breathing chamber as the exhalation force is applied.

The EVS can be used to treat patients suffering from, among other ailments, respiratory illnesses such as Covid-19 (a.k.a. coronavirus). The EVS, much like a traditional ventilator, moves air into and out of the lungs thus delivering breathable oxygen to patients unable to breathe sufficiently on their own. The EVS provides the patient's medical team the ability to adjust the breathing patterns and volumes of the EVS to fit the particular needs of the patient. Additionally, the EVS contains basic alarm functions that notify a patient's medical team when there is a loss of pressure or low oxygen in the patient's breathing loop.

Unlike a traditional mechanical ventilator, the EVS is designed specifically for emergency situations. Therefore, it does not contain features that are commonly used in non-emergency situations such as during surgical procedures. The EVS is therefore considerably less expensive than traditional ventilators. The EVS is lightweight, portable (carried by hand), and thus is easy to transport and use in unconventional settings including triage centers and non-medical facilities. Additionally, unlike a traditional ventilator, different oxygen or other gas sources can easily and quickly be interchanged, thus allowing a patient's medical team to make quick adjustments to the patient's treatment.

The EVS is an open-circuit ventilator that provides mechanical ventilation for intubated patients. The EVS is agnostic with regard to the patient breathing loop. EVS is a positive displacement piston-driven ventilator. The EVS, in different operating modes, can use filtered air, enriched air (e.g., either air or 100% oxygen to maintain a minimum pressure inside of the patient breathing loop), or 100% oxygen for breathing media. The pressure is maintained by a transducer (such as a Balluff transducer operating at −1 to +2 PSI).

The transducer feeds information to a computer (or processor) controlled solenoid valve that injects oxygen into the patient breathing loop. The patient breathing loop is isolated from the positive displacement piston by two silicone mushroom valves or check valves as described further below. Note that providing two valves, rather than only one valve, isolates the machine from potential contamination (such as by an infectious disease or virus such as COVID-19) and eases de-contamination requirements.

The positive displacement piston mechanism is made using a nitrile rolling seal diaphragm that is mounted onto a piston. The piston draws air through a filter (such as a p100 filter) for the air/enriched air application shown in FIG. 4, and as shown in FIG. 3 for the 100% oxygen operation, oxygen gas is injected through a demand regulator capable of maintaining a flow rate of 30 liters per minute (LPM).

Referring now to FIGS. 1A, 1B, 1C, and 1D, top, perspective, front, and side views, respectively, of the EVS are shown according to embodiments of the invention. Referring to FIG. 2, arrows 200 and 208 demonstrate the gas flow through the filter and/or oxygen regulator 202 (from an air source) through check valves 204 and 206 into the breathing chamber 210 when the motor 220 is controlled to cause the piston 214 to increase the space in the breathing chamber 210. This is during patient exhalation. The gas flow, as illustrated by arrows 228 and 238 then moves through the check valve 230, past the oxygen sensor 232 and oxygen addition port 240, through a second check valve 234 and to the air output of the EVS as shown by arrow 238 as the piston. This is during patient inhalation. The oxygen sensor 232 senses the oxygen content of the air flow between the two check valves 230 and 234, and the oxygen addition port 240 enables addition of oxygen to the air flow between the two check valves 230 and 234. The air output from the EVS may then move through conditioning external to the EVS, such as by humidifier. There is a pressure transducer 236 external (in relation to the air flow direction as illustrated by arrow 238) to the second check valve 234 of the output of the EVS for sensing pressure.

The work of the piston back-and-forth, or piston movement, is illustrated by arrow 226. The motor 220 drives the piston via lead screw 216, which is attached using lead screw nut 218. A rolling seal 212 seals the breathing chamber 210 as the piston moves according to arrow 226. Guide rods 222, such as the one shown in FIG. 2 guide the movement of the piston back-and-forth. In one embodiment, three (3) guide rods 222 are utilized. The guide rod 222 is attached using a guide rod bearing 224.

Referring now to FIG. 3, a 100% oxygen mode 300 of the EVS is shown. Mode 300 enables 100% oxygen to be output by the EVS as illustrated by arrows 310. As shown, an oxygen supply 308 is connected to oxygen addition port 306, which is connected in the air flow path of the system. The piston 312 works as discussed elsewhere herein to cause the breathing chamber 314 to increase and decrease in volume. A pressure transducer 304 is used to sense the pressure of the system. In this mode 300, an oxygen injection solenoid 302 is disabled, because the system is running on 100% oxygen and there is no need for oxygen to be added to the system based on controlled feedback to maintain a certain percentage of oxygen.

Referring now to FIG. 4, an oxygen enriched mode 400 of the EVS is shown. Mode 400 enables oxygen enriched air to be output by the EVS as illustrated by arrows 410. Such oxygen enriched air would be any air that includes less than 100% oxygen content. As shown, the piston 412 works to increase and decrease the volume of the breathing chamber 414 as discussed elsewhere herein. The oxygen injection solenoid 402 is used to inject oxygen at the desired rate to cause the air to have a certain oxygen content. In one embodiment the oxygen injection solenoid 402 is a six volt direct current (6 V-DC) solenoid. The system includes a mounted inlet filtration device 406 that enables inflow of environmental air in the direction of arrow 408 to the system. Such air is oxygen infused as discussed, and the pressure transducer 404 measures pressure at the output of the system, where oxygen enriched air flows.

Referring now to FIG. 5, a method for generating an EVS and providing mechanical ventilation to a patient is illustrated. The first step, as illustrated by block 502, is to generate an exterior housing, chamber housing, piston, stand (and in some cases other, additional components, and in some cases nearly all or all components of the EVS) by injection molding and/or three-dimensional (3D) printing. The next step, as illustrated by block 504, is to build an emergency ventilator system (EVS) using the generated components.

The next step, as illustrated by block 506, is to provide mechanical ventilation for the patient using the EVS. The mechanical ventilation may be accomplished by computer control of the motor driving the piston in the EVS. Further, oxygen is regulated by feedback from the oxygen sensor disposed near the air output of the EVS. The computer or controller may be connected to a display and input device, which may be attached to the exterior housing of the EVS for ease of use as shown in other figures.

Referring now to FIGS. 6-16, various diagrams and expanded views of components of embodiments of the EVS are illustrated. FIG. 6 illustrates another embodiment of the EVS 100 in full assembly. A case shell 602 provides a housing for the EVS. A user interface 604 receives input from users and provides information to users. A regulator assembly port 606 provides external connection for the regulator sub-assembly. A handle 608 is also provided.

Referring now to FIG. 7, the EVS 100, 700 is shown in expanded view with major sub-assemblies expanded. The regulator sub-assembly 702 provides air regulation for the EVS. A regulator gasket 704 is between the regulator sub-assembly 702 and the cylinder lid sub-assembly 706. The piston sub-assembly 708 connects to the cylinder lid sub-assembly 706 and fits inside the cylinder riser sub-assembly 712. The cylinder riser sub-assembly 712 is connected to the stand sub-assembly 716. The motor sub-assembly 718 connects to the piston sub-assembly 708 through the stand sub-assembly 716 and the cylinder riser sub-assembly 712. A baseplate sub-assembly 720 forms a base for the EVS.

An enlarged view of the stand sub-assembly 716 is shown in FIG. 8.

FIGS. 9A, 9B, and 9C, respectively, show an exploded view, a side view, and a cross-section of the piston sub-assembly 708. The piston 214 is shown with the rolling seal 212 attached. Three guide rods 900 are used in this embodiment. A lead screw nut 902 is used to connect the piston sub-assembly 708 with the lead screw of the motor sub-assembly (shown elsewhere).

FIGS. 10A and 10B, respectively, show an exploded view and a perspective view of the baseplate sub-assembly 720. Rivet nuts 1004 are inserted into the baseplate subassembly 720 and connect the rubber feet 1002 to the baseplate sub-assembly 720.

FIGS. 11A, 11B, 12A, and 12B, respectively, show an exploded view, a perspective view, an end view, and a cross-section of the regulator sub-assembly 702. A regulator nozzle 1112 connects with a mushroom valve 1110 and mushroom valve cage 1108. An o-ring 1106 helps by providing a seal. The regulator body 1104 houses the regulator sub-assembly 702 components. A regulator poppet assembly 1114 may be connected with a regulator adjustment assembly 1116. A diaphragm strike plate 1118 is adjacent the diaphragm 1120 and diaphragm shield 1122, which are enclosed in the regulator body 1104 by the regulator cap 1124.

Referring now to FIG. 13, an exploded view of the cylinder riser sub-assembly 712 is shown. The cylinder riser 1302 receives a number of rivet nuts 1304, which as shown at callout 1306, are installed from the top side.

FIGS. 14A and 14B, respectively, show an exploded view and a perspective view of the cylinder lid sub-assembly 706. A cylinder lid 1402 receives a number of rivet nuts 1408, which are installed from the top side as shown by callout 1410. The over pressure valve (OPV) 1404 is installed from the bottom as shown by callout 1406.

FIGS. 15A, 15B, and 15C, respectively, show the motor sub-assembly 718 in exploded, side, and cross section. The motor 1502 is connected to the shaft coupling 1504 and the lead screw 1506.

FIGS. 16A, 16B, 16C, and 16D, respectively, show a perspective front view, a perspective front view with accessories, a perspective side view with accessories, and a rear view, of an embodiment of the EVS. FIG. 16D shows an on-off switch 1602, a data port 1604, a power port 1606, and an information screen 1608.

Embodiments of the present invention described above, with reference to flowchart illustrations and/or block diagrams of methods or apparatuses (the term "apparatus" including systems and computer program products), will be understood to include that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a particular machine, such that the instructions, which execute via the processor of the computer or other programmable data processing apparatus, create mechanisms for providing emergency ventilation for patients and implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer readable memory produce an article of manufacture including instructions, which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions, which execute on the computer or other programmable apparatus, provide steps for implementing the functions/acts specified in the flowchart and/or block diagram block or blocks. Alternatively, computer program implemented steps or acts may be combined with operator or human implemented steps or acts in order to carry out an embodiment of the invention.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations, modifications, and combinations of the just described embodiments can be configured without departing from the scope and spirit of the invention. Therefore, it is to be understood that, within the scope of the appended claims, the invention may be practiced other than as specifically described herein.

What is claimed is:

1. An emergency ventilator system for mechanical ventilation of a patient, the emergency ventilator system comprising:
    a chamber housing defining a breathing chamber;
    a piston;
    a motor operably connected to the piston, the motor configured to apply an exhalation force to move the piston in an exhalation direction corresponding to the patient's exhalation and to apply an inhalation force to move the piston in an inhalation direction corresponding to the patient's inhalation;
    wherein the piston increases an amount of air in the breathing chamber as the exhalation force is applied and decreases the amount of air in the breathing chamber as the inhalation force is applied;
    at least one exhalation check valve disposed between an air source and the breathing chamber, the at least one exhalation check valve configured to allow airflow from the air source to the breathing chamber as the exhalation force is applied and not to allow airflow from the breathing chamber to the air source as the inhalation force is applied;
    at least one inhalation check valve disposed between the breathing chamber and an air output, the at least one inhalation check valve configured to allow airflow from the breathing chamber to the air output as the inhalation force is applied and not to allow airflow from the air output to the breathing chamber as the exhalation force is applied, the at least one inhalation check valve comprising at least a first inhalation check valve and a second inhalation check valve connected in series with one another between the breathing chamber and the air output;
    an oxygen sensor disposed between the first inhalation check valve and the second inhalation check valve; and
    an oxygen addition port disposed between the first inhalation check valve and the second inhalation check valve, the oxygen addition port for receiving oxygen and infusing the airflow with the received oxygen.

2. The emergency ventilator system of claim 1, wherein:
    each of the chamber housing and piston are generated by an injection molded or three-dimensional (3D) printing method, thereby enabling a quick manufacture of the emergency ventilator system.

3. The emergency ventilator system of claim 1, wherein:
    the at least one exhalation check valve comprises at least a first exhalation check valve and a second exhalation check valve connected in series with one another between the air source and the breathing chamber.

4. The emergency ventilator system of claim 1, wherein the oxygen sensor senses an oxygen level of the airflow and the oxygen addition port infuses oxygen into the airflow based at least in part on the oxygen level sensed by the oxygen sensor.

5. The emergency ventilator system of claim 1, further comprising: an exterior housing configured to enclose the motor, piston, and chamber housing.

6. The emergency ventilator system of claim 5, wherein the exterior housing is generated by an injection molded or three-dimensional (3D) printing method, thereby enabling a quick manufacture of the emergency ventilator system.

7. The emergency ventilator system of claim 1, further comprising:
- a rolling seal disposed between the piston and sides of the chamber housing, the rolling seal configured to seal the chamber housing to ensure the breathing chamber retains air pressure necessary to generate air flow through the check valves as exhalation force is applied and as the inhalation force is applied.

8. The emergency ventilator system of claim 1, further comprising:
- a lead screw operatively connected to the motor and configured to transfer the exhalation force and the inhalation force to the piston.

9. The emergency ventilator system of claim 1, further comprising:
- a pressure transducer disposed between the second inhalation check valve and the air output, the pressure transducer for measuring an output pressure of the emergency ventilator system; and
- an electrical connection configured to operably connect the motor, the oxygen sensor, and the pressure transducer to a processor configured to control operation of the emergency ventilator system in order to replicate natural ventilation of the patient.

* * * * *